United States Patent [19]

Stoller

[11] Patent Number: 4,495,949
[45] Date of Patent: Jan. 29, 1985

[54] TRANSILLUMINATION METHOD

[75] Inventor: Milton Stoller, West Hartford, Conn.

[73] Assignee: Spectrascan, Inc., So. Windsor, Conn.

[21] Appl. No.: 620,272

[22] Filed: Jun. 13, 1984

Related U.S. Application Data

[62] Division of Ser. No. 399,866, Jul. 19, 1982, Pat. No. 4,467,812.

[51] Int. Cl.³ .............................................. A61B 6/12
[52] U.S. Cl. ................................... 128/664; 128/665; 128/23; 128/303.1
[58] Field of Search ........................................ 128/4–8, 128/660, 665, 303.1, 23; 362/32, 66–68, 321; 358/81–82, 98, 110, 113

[56] References Cited

U.S. PATENT DOCUMENTS

| | | | |
|---|---|---|---|
| 738,707 | 9/1903 | Van Nort | 362/321 |
| 3,136,310 | 6/1964 | Meltzer | 128/6 |
| 3,710,011 | 1/1973 | Altemus et al. | 358/82 |
| 3,748,471 | 7/1973 | Ross et al. | 358/113 |
| 4,048,493 | 9/1977 | Lee | 362/321 |
| 4,086,616 | 4/1978 | Catano et al. | 358/113 |
| 4,123,172 | 10/1978 | French | 362/32 |
| 4,170,987 | 10/1979 | Anselmo et al. | 128/665 |
| 4,212,306 | 7/1980 | Mahmud | 128/665 |
| 4,253,447 | 3/1981 | Moore et al. | 128/6 |
| 4,259,948 | 4/1981 | Urban | 128/6 |
| 4,261,344 | 4/1981 | Moore et al. | 128/6 |
| 4,286,602 | 9/1981 | Guy | 128/665 |
| 4,290,433 | 9/1981 | Alfano | 128/665 |
| 4,312,357 | 1/1982 | Andersson et al. | 128/665 |
| 4,331,132 | 5/1982 | Mukasa | 128/6 |
| 4,365,307 | 12/1982 | Tatsuwaki et al. | 358/110 |

OTHER PUBLICATIONS

Brooks et al., "Color Display System" *IBM Technical Disclosure Bulletin* vol. 10, No. 3, Aug. 1967, pp. 226–228.

*Primary Examiner*—William E. Kamm
*Assistant Examiner*—Mitchell J. Shein

[57] ABSTRACT

A non-destructive testing technique, particularly suitable for the non-invasive examination of human body tissue, wherein the object of interest is transilluminated with multi-wavelength light. Apparatus for practicing the technique generates transillumination light containing different colors and the light which passes through the tissue is divided and filtered to provide plural light beams lying in separate wavelength ranges. These light beams are detected by a video system which provides information bearing signals to data processing circuitry which determines the transmissivity at each wavelength of each point of the object within the viewing field.

11 Claims, 1 Drawing Figure

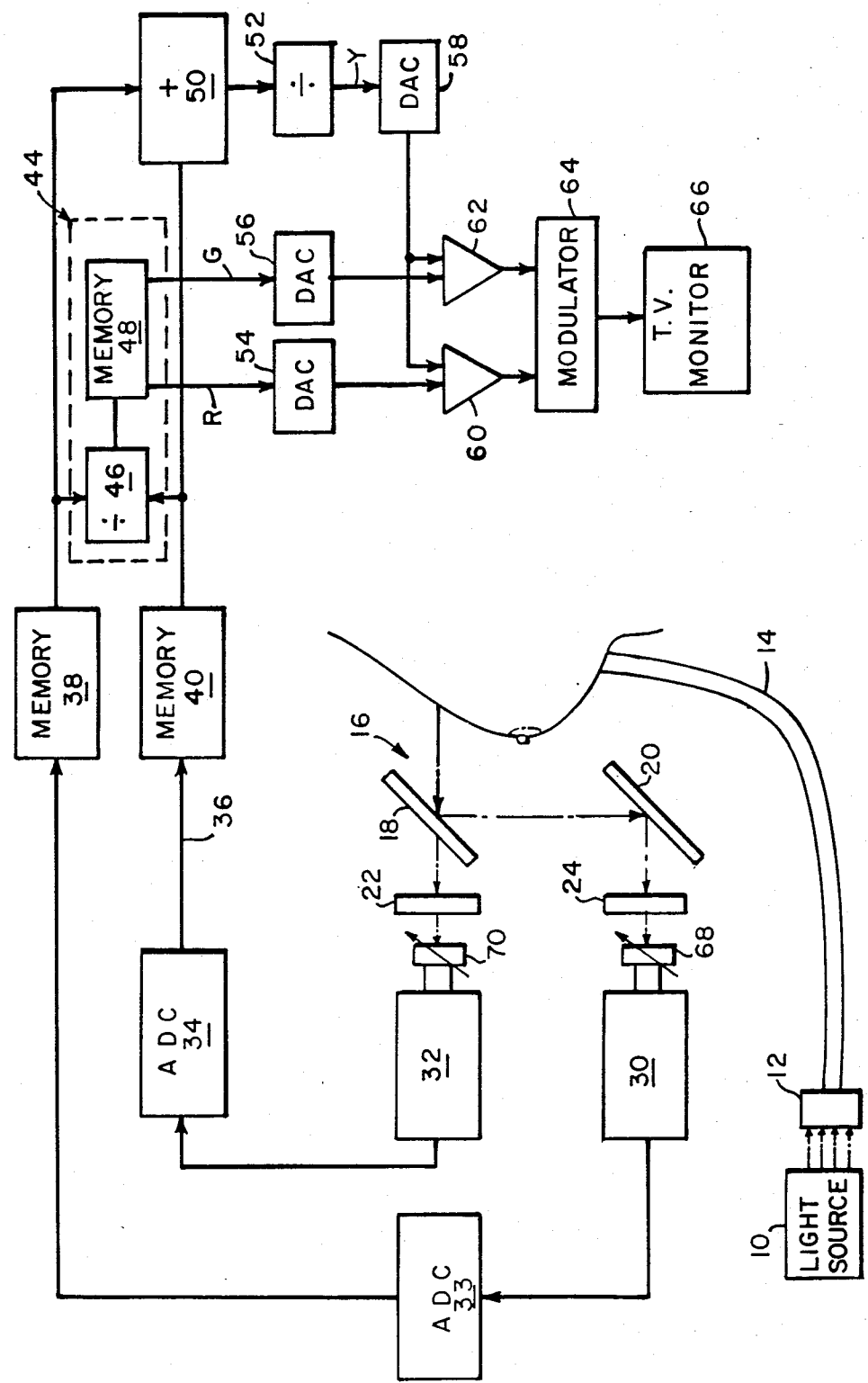

TRANSILLUMINATION METHOD

This is a division of application Ser. No. 399,866, filed, July 19, 1982 now U.S. Pat. No. 4,467,812.

BACKGROUND OF THE INVENTION (1) Field of the Invention

The present invention relates to non-destructive testing and particularly to a medical diagnostic technique which requires neither invasion of the body or the use of ionizing radiation. More specifically, this invention is directed to transillumination and especially to creating a display which is indicative to the amount of absorption at each point in the object of light having a plurality of preselected different wavelengths. Accordingly, the general objects or the present invention are to provide novel and improved methods of such character.

(2) Description of the Prior Art

While not limited thereto in its utility, the present invention has particular significance as a breast examination device and method. At the present time there is no accepted procedure, other than palpation by a physician, which may be employed for the routine screening of patients, particularly those under the age of fifty, in an effort to diagnose breast cancer. The most widely accepted current diagnostic technique comprises mammography which, because it requires the use of ionizing, i.e., X-ray, radiation, is customarily employed only subsequent to palpation having revealed an apparent abnormality.

Other non-invasive examination techniques which are available include thermography and echography. Both of these techniques have been found to be only very limited utility and thus their application has largely been to supplement information obtained through the use of mammography.

It has also been proposed to utilize transillumination, i.e., the passing of light through tissue, in order to diagnose abnormalities. Prior transillumination techniques and apparatus are disclosed in U.S. Pat. Nos. 3,127,115, 3,371,202, 3,527,932, 3,674,008, 3,711,700, 3,732,416, 3,769,963, 4,077,399, 4,212,306 and 4,286,602. Transillumination, which is also known in the art as diaphanography or diaphanoscopy, is also discussed in Russian Pat. Nos. 279,879 and 591,178 as well as the publication "Diaphanologie mammaire" by C. Gros et al. which appeared in J. Radiol Electrol., 1972, Vol. 53, No. 4, pp. 297–306 and the article "Etude diphanoscopique des alteration dystrophiques du sein" by C. Di Maggio et al which appeared in Senologia, June 1978, No. 2, pp. 69–71. The potential advantages of transillumination versus the above-mentioned other non-invasive examination techniques are discussed in detail in U.S. Pat. No. 4,286,602.

Initial efforts to employ transillumination relied upon visual observation of the light which passed through the tissue under study. These efforts were largely unsuccessful since the human eye is not sensitive to light at the frequencies which pass through human body tissue, i.e., principally wavelengths in the range of 600 to 1500 nanometers. Light having a wavelength below 600 nanometers is largely absorbed by human body tissue while light at wavelengths above 1500 nanometers is largely absorbed by water in the tissue. The difficulty in obtaining useful information by visual observation was increased by the fact that the examination had to be performed in a darkened room and it is well known that the sensitivity of the eye to light having a wavelength within the range of interest decreases in a dark environment.

The major problems incident to visual observation were overcome when infrared light sensitive film became available. However, the use of photographic techniques employing infrared film, like the use of X-rays, does not provide information in real time. Further, since the light source and tissue under examination must be manipulated in order to insure that all regions within the tissue will be seen, and if necessary or desirable seen from different viewing angles, an examination which included recording information on film required either the taking of many pictures or was very time-consuming in that the patient had to wait while the initially taken pictures were developed and viewed so that additional pictures could be taken if necessary.

A recent improvement in transillumination technology employs a TV camera which is sensitive to light in the red and near infrared regions, i.e., in the range of 600 to perhaps 1200 nanometers. The use of a TV camera permits real time imaging and provides results which are believed to be at least comparable to those achieved through mammography but without the use of ionizing radiation. Nevertheless, there is a desire to enhance the capability of presently available transillumination devices and particularly to form an image characterized by tissue differentiation, i.e., to provide output information which is indicative of the type of tissue being illuminated.

SUMMARY OF THE INVENTION

The present invention comprises a novel and improved transillumination technique, particularly a method well suited for the examination of body tissue, and apparatus for use in the practice of that novel technique. In accordance with the present invention the tissue or other object being examined is illuminated with light from a multi-wavelength source. Information commensurate with the light which passes through the tissue at each of a plurality of preselected illumination wavelengths is stored and the stored information subsequently employed to produce an image which represents the absorption characteristics of the tissue which has been illuminated.

Apparatus in accordance with the present invention includes a source of transillumination light comprising different frequencies, i.e., light lying within different pre-selected bands of frequency. In accordance with one embodiment, the light source provides radiation which includes light having wavelengths lying in the red and near infrared regions. The tissue under examination is illuminated and the light which passes through the tissue is divided, separately filtered and sensed by a video system comprising a camera associated with each filter. The outputs of the cameras are a series of signals corresponding to images of the tissue as illuminated by the light at the different selected wavelengths. These video signals are separately stored and subsequently employed to form a composite image.

Also in accordance with the preferred embodiment, the information commensurate with the stored images is employed to produce a display wherein each point of the display contains information characteristic of the ratio of the light within each frequency band which has passed through the tissue at a corresponding point. Thus, by way of example, a color may be assigned to each ratio and a multi-color image formed.

BRIEF DESCRIPTION OF THE DRAWING

The present invention may be better understood and its numerous objects and advantages will become apparent to those skilled in the art by reference to the accompanying drawing which is a functional block diagram of apparatus in accordance with a first embodiment of the invention.

DESCRIPTION OF THE PREFERRED EMBODIMENT

With reference now to the drawing, in the disclosed embodiment "white" light, i.e., light included wavelengths in the red and near infrared spectra, is employed for transilluminating human body tissue. Light at the different wavelengths chosen will be absorbed by the tissue as a function of wavelength and tissue type. In accordance with one embodiment of the present invention "white" light is generated by a lamp 10. The light produced by lamp 10 is collected by a condensing lens system 12 which focus the light at the end of a fiber optic bundle 14.

In examining a breast, as depicted in the drawing, the free end of fiber optic bundle 14 is placed in contact with the skin to produce a source of transilluminating light. During transillumination a first element of a beam splitter, indicated generally at 16, is positioned so that light passing through the breast or other object being examined will fall on the face thereof. In the disclosed embodiment the beam splitter 16 comprises mirrors 18 and 20. One half of the light incident on the face of mirror 18 which is directed toward the light source will pass through the mirror while the other half of the incident light will be reflected to mirror 20. The light passing through mirror 18 is, in turn, passed through a filter 22. The light reflected from mirror 20 is directed through a filter 24. Filter 22, in the embodiment being described, will pass only wavelengths in the 650-750 nanometer, i.e., red, region. Filter 24 will pass light only in the 750-850 nanometer, i.e., near infrared, region.

Filters 22 and 24 are respectively positioned directly in front of the lens assemblies of respective video cameras 32 and 30. In the embodiment being described the cameras 32 and 30 will include a silicon faceplate tube that is responsive in the region from 650 nanometers to 900 nanometers. The camera tubes may, for example, comprise silicon diode array type devices available from RCA under the trademark "ULTRICON". The light received by the cameras will have the effect of discharging, in varying degrees, the surface of the video camera tubes. Scanning of the tube surfaces by an electron beam produces, in the conventional manner, a video output signal. The analog output signals from cameras 32 and 30 are respectively delivered as the inputs to analog-to-digital convertors 34 and 33. The digitally coded signals from convertors 34 and 33 are supplied to respective frame memories 40 and 38. The memories 40 and 38 may, for example, comprise dynamic memory elements having 8 bits of memory for each picture location, i.e., each pixel. The operation of cameras 32 and 30 as well as the read out of memories 40 and 38 will be synchronized.

In operation of the system described above, "red" light which is not absorbed by the object under examination will be passed by filter 22 to camera 32 and a signal commensurate with the intensity of the red light will be stored in memory 40. Thus, memory 40 will contain information commensurate with the degree of absorption of red light by, for example, the breast tissue at each point within the viewing field, i.e., a number will be stored in memory 40 which is commensurate with the energy content of the transilluminated "red" light. Similarly, the light in the near infrared region which is passed through the test object will be delivered to camera 30 and a signal commensurate therewith stored in memory 38. Memory 38 will thus contain information commensurate with the degree of absorption of light i.e., the energy content of the transilluminated light in the near infrared region of the test object.

The information in memories 38 and 40 is simultaneously read by an encoder which is indicated generally at 44. In actual practice, encoder 44 will comprise a RAM which functions as a look-up table. To facilitate understanding of the disclosed embodiment of the invention, encoder 44 has been functionally depicted as a divider 46 and a memory 48. The memory 48 will have, for example, $2^8 \times 2^8$ addresses and numbers corresponding to the intensity of two colors, typically red and green, commensurate with ratios of the numbers i.e., the relative energy content of the light at the wavelengths of interest which has passed through each point in the tissue under examination, which may be stored at each pixel in memories 38 and 40 will be stored at the memory locations in memory 48. The data stored in memories 38 and 40 will be read by memory 48 at twice the rate of loading of memories 38 and 40. The numbers stored at the corresponding memory locations in memories 38 and 40 are employed to address memory 48 and memory 48 will produce a pair of color related, digitally coded output signals for each pixel. This is functionally equivalent to dividing the numbers stored at the memory locations in memories 38 and 40 in the divider 46 and employing the thus produced ratio to address memory 48. The numbers which are read out of memory 48 comprise digitally coded chrominance signals which, in the example being described, will correspond to a red "R" intensity and a green "G" intensity.

The numbers read from memories 38 and 40 are also applied to and adder 50 where they are summed. The output of adder 50 is delivered to a divide by two circuit 52. The output of divider 52 is a digitally encoded average luminance or "Y" signal.

The "R" and "G" chrominance signals from memory 48 are converted to analog form by means of digital-to-analog converters 54 and 56 while the average luminance signal is converted to analog form by digital-to-analog converter 58. The outputs of converters 54 and 56 are respectively applied at first inputs to differential amplifiers 60 and 62. The second input to amplifiers 60 and 62 is the luminance signal from converter 58. The combined luminance and chrominance signals appearing at the outputs of amplifiers 60 and 62 are applied to a standard TV modulator 64. Modulator 64 provides a composite color video signal which is delivered to a TV monitor 66. This composite signal will, in the customary fashion, provide horizontal sync, color burst and color modulation information for each frame.

It is to be noted that, in the interest of reducing the size of the look-up memory, the encoder 44 may look at the most significant six bits of the signals stored in memories 38 and 40 while the adder 50 will look at all eight bits of the stored data.

It is also to be noted that the present invention may be employed as an analytical tool wherein the ratio of the absorption by the object under examination of light at the selected transillumination frequencies at any point of interest may be read out and displayed on monitor 66. The amount of absorption of different color light varies with the nature of the tissue being transilluminated even in the case of normal tissue. Accordingly, it has been found desirable to initially perform a "normalizing" or "balancies" step when practicing the present invention. Since the absorption of light in the red and near infrared regions will vary with the characteristic of the tissue under examination, for example as a function of whether the tissue is glandular or fatty, an initial adjustment will typically be made so that normal tissue will be displayed as a pre-selected color or colors. Thus, in a typical case, the image of tissue which has been determined to be normal for the patient being tested may be displayed as a white and black image while abnormalities may be represented by color. In accordance with the disclosed embodiment of the invention the above-discussed step of "normalizing" is achieved through use of the "f-stop" controls, indicated schematically at 68 and 70, which form standard portions of the lens assemblies of vidicons 30 and 32. As noted above, the "normalization" procedure will typically be performed so as to cause all normal tissue to appear in white on a black background. Thus, at the onset of each examination, the apparatus will be adjusted so that transillumination of the patient's normal tissue will result in cameras 30 and 32 receiving light of equal intensity during the illumination of the tissue.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. A non-invasive and non-destructive examination method comprising the steps of:
    illuminating the object to be examined with light comprising at least two different wavelengths;
    detecting light at each of said at least two different wavelengths which has passed through the illuminated object;
    recording information commensurate with the intensity of the detected light at each of said at least two different wavelengths, the information commensurate with the same points in the illuminated object being recorded at simultaneously readable locations;
    storing display correlated data values for each of a plurality of ratios of the information commensurate with the detected light at each of said at least two different wavelengths which may be recorded;
    employing said recorded information for the same points in the illuminated object to select stored display correlated data values; and
    employing the thus selected display correlated data values read to produce a display which represents the absorption characteristics of the object at the said at least two different wavelengths.

2. The method of claim 1 wherein the step of detecting comprises:
    filtering the light passing through the object to produce light lying within two frequency bands; and
    wherein the step employing said recording information to select display correlated data values includes:
    calculating the ratio of the light at the said at least two different wavelengths which is absorbed within the object for each illuminated point.

3. The method of claim 2 wherein the step of producing a display comprises:
    assigning intensity levels for two different colors for each display correlated data value; and
    modulating a color television display with the assigned intensity levels.

4. The method of claim 1 wherein the step of producing a display comprises:
    assigning intensity levels for two different colors for each display correlated data value; and
    modulating a color television display with the assigned intensity levels.

5. The method of claim 1 wherein the step of detecting comprises:
    dividing the light passing through the object into two beams;
    separately filtering each beam to produce light lying within two frequency bands;
    sensing the filtered beams with television cameras to produce image frames commensurate with the intensity of the light at each of said at least two different wavelenths which has passed through each point of the object; and
    encoding the information corresponding to each image frame.

6. The method of claim 5 wherein the step of employing said recorded information to select display correlated data values includes:
    calculating the ratio of the light at said at least two different wavelengths which is absorbed at each point in the object.

7. The method of claim 6 wherein the step of producing a display comprises:
    assigning intensity levels for two different colors for each display correlated data value; and
    modulating a color television display with the assigned intensity levels.

8. The method of claim 1 wherein the object being examined is comprised of body tissue and said method further comprises the step of:
    varying the ratio of the information commensurate with the detected light whereby the said information commensurate with the light at each of said at least two different wavelengths which has passed through each point in the illuminated tissue will be caused to have a selected relationship when tissue of a selected type is illuminated.

9. The method of claim 8 wherein the step of detecting comprises:
    dividing the light passing through the tissue into two beams;
    separately filtering each beam to produce light lying within two frequency bands;
    sensing the filtered beams with television cameras to produce image frames commensurate with the intensity of the light at each of said at least two different wavelengths which has passed through each point in the tissue; and
    encoding the information corresponding each image frame.

10. The method of claim 9 wherein the step of varying the information ratio comprises:
    selectively adjusting the amount of light passed to the individual television cameras.

11. The method of claim 10 wherein the step of producing a display comprises:
    modulating a color television display with the display correlated data values, the light detected by the cameras being varied so as to cause tissue of a selected type to be displayed in a preselected color.

* * * * *